US00PP31087P2

(12) United States Plant Patent
Knosher

(10) Patent No.: US PP31,087 P2
(45) Date of Patent: Nov. 19, 2019

(54) ***VERONICA* PLANT NAMED 'BALVEREVLU'**

(50) Latin Name: *Veronica longifolia*
Varietal Denomination: Balverevlu

(71) Applicant: Ball Horticultural Company, West Chicago, IL (US)

(72) Inventor: Lynne Knosher, St. Charles, IL (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/999,989

(22) Filed: Sep. 6, 2018

(51) Int. Cl.
*A01H 5/02* (2018.01)
*A01H 6/50* (2018.01)

(52) U.S. Cl.
USPC ..... Plt./251
CPC ..... *A01H 6/50* (2018.05)

(58) Field of Classification Search
USPC ..... Plt./251
See application file for complete search history.

(56) References Cited

PUBLICATIONS

UPOV hit on a *Veronica* plant named 'Forever Blue', QZ PBR 20182993, filed Nov. 14, 2018.*

* cited by examiner

*Primary Examiner* — Anne Marie Grunberg
(74) *Attorney, Agent, or Firm* — Audrey Charles

(57) ABSTRACT

A new and distinct cultivar of *Veronica* plant named 'Balverevlu', characterized by its deep violet-blue colored flowers, medium green-colored foliage, and vigorous, upright-mounded growth habit, is disclosed.

1 Drawing Sheet

Latin name of genus and species of plant claimed: *Veronica longifolia.*

Variety denomination: 'Balverevlu'.

BACKGROUND OF THE INVENTION

The present invention relates to a new and distinct cultivar of *Veronica* plant botanically known as *Veronica longifolia* and hereinafter referred to by the cultivar name 'Balverevlu'.

The new cultivar originated in a controlled breeding program in Elburn, Ill., during July 2012. The objective of the breeding program was the development of *Veronica* cultivars having a long flowering season.

The new *Veronica* cultivar was the result of open-pollination. The female (seed) parent of the new cultivar is the proprietary *Veronica longifolia* breeding selection coded 5612-1-A5, not patented, characterized by its medium violet-blue colored flowers, medium green-colored foliage, and vigorous, upright growth habit. The male (pollen) parent of the new cultivar is unknown. The new cultivar was discovered and selected as a single flowering plant within the progeny of the above stated open-pollination during June 2013 in a controlled environment in Elburn, Ill.

Asexual reproduction of the new cultivar by terminal stem cuttings since June 2013 in Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balverevlu' as a new and distinct cultivar of *Veronica* plant:

1. Deep violet-blue colored flowers;
2. Medium green-colored foliage; and
3. Vigorous, upright-mounded growth habit.

Plants of the new cultivar differ from plants of the female parent primarily in having a darker flower color, no visible pollen, and increased branching.

Of the many commercially available *Veronica* cultivars, the most similar in comparison to the new cultivar is MOODY BLUES Dark Blue 'Novaverblu', U.S. Plant Pat. No. 26,602. However, in side by side comparisons, plants of the new cultivar differ from plants of 'Novaverblu' in at least the following characteristics:

1. Plants of the new cultivar have a darker flower color than plants of 'Novaverblu';
2. Plants of the new cultivar have wider mature leaves than plants of 'Novaverblu'; and
3. Plants of the new cultivar have a flower bud color that is different from plants of 'Novaverblu'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balverevlu'. The plants were approximately four months old. The plants were grown in one-gallon containers for approximately 9 weeks in a greenhouse in Elburn, Ill. followed by 3 weeks in an open-sided polyhouse in West Chicago, Ill. Plants were given two pinches, one at one week before transplant and one two weeks after transplant.

DETAILED BOTANICAL DESCRIPTION

Figure 1:
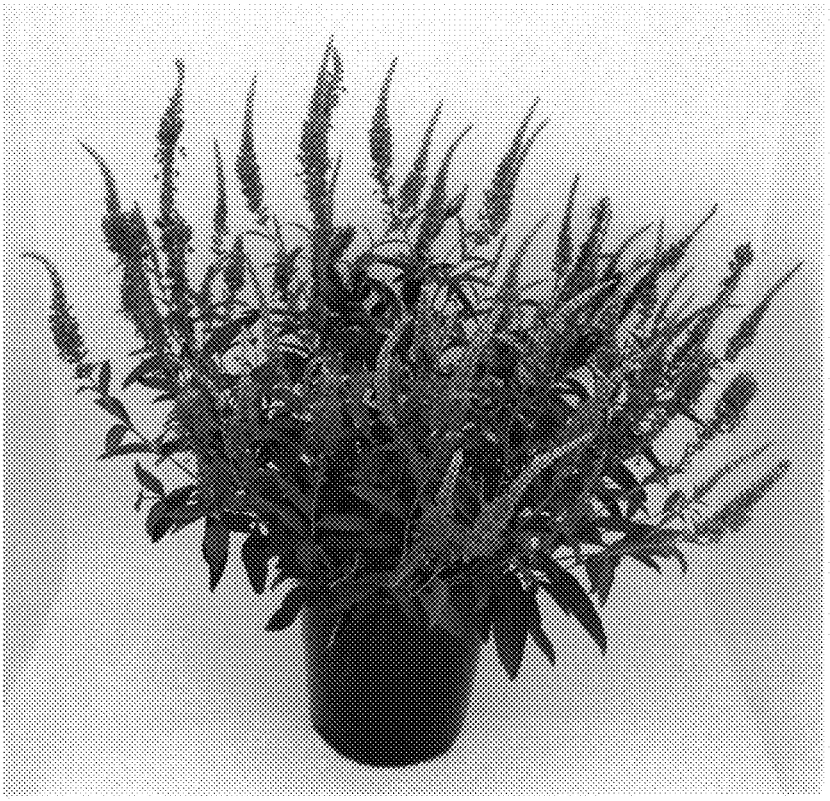
FIG. 1 illustrates a side view of the overall growth and flowering habit of 'Balverevlu'.
Figure 2:
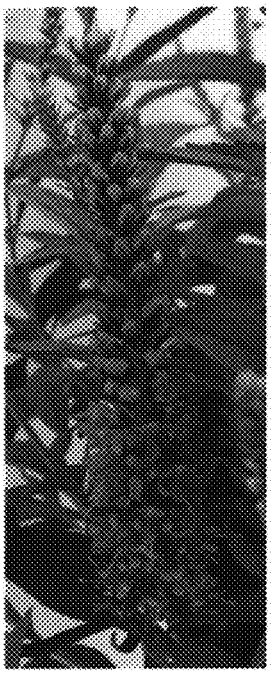
FIG. 2 illustrates a close-up view of the inflorescences of 'Balverevlu'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2018 under natural light conditions in West Chicago, Ill.

The following descriptions and measurements describe approximately four-month old plants produced from cuttings from stock plants and grown under conditions comparable to those used in commercial practice. The plants were grown in one-gallon containers for approximately 9 weeks in a greenhouse in Elburn, Ill. followed by 3 weeks in an open-sided polyhouse in West Chicago, Ill. Plants were given two pinches, one at one week before transplant and one two weeks after transplant. Greenhouse temperatures in Elburn, Ill. were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Veronica longifolia* 'Balverevlu'.

Parentage:

*Female parent.*—Proprietary *Veronica longifolia* breeding selection coded 5612-1-A5, not patented.

*Male parent.*—Unknown.

Propagation:

*Type cutting.*—Terminal stem.

*Time to initiate roots.*—Approximately 7 to 10 days.

*Time to produce a rooted cutting.*—Approximately 5 to 6 weeks.

*Root description.*—Fibrous.

*Rooting habit.*—Freely branching.

Plant description:

*Commercial crop time.*—Approximately 10 to 12 weeks from a rooted cutting to finish in a 15 cm pot. Vernalization to initiate flowering is not required.

*Growth habit and general appearance.*—Herbaceous perennial, vigorous, upright-mounded.

*Hardiness.*—USDA Zone 5a (−20° F. to −15° F./−28.9° C. to −26° C.).

*Size.*—Height from soil level to top of plant plane: Approximately 38.0 cm. Width: Approximately 46.0 cm.

*Branching habit.*—Freely branching, pinching enhances basal branching. Quantity of main branches per plant: Approximately 6.

*Branch.*—Strength: Moderate. Branch height to bottom on inflorescence: Approximately 19.5 cm. Diameter: Approximately 3.0 mm. Length of central internode: Approximately 3.0 cm. Texture: Moderately pubescent. Color of young stems: 146C. Color of mature stems: 146C, becoming woody 200D with age.

Foliage description:

*General description.*—Quantity of leaves per main branch: Approximately 12. Fragrance: None detected. Form: Simple. Arrangement: Opposite.

*Leaves.*—Aspect: Perpendicular to stem. Shape: Elliptic to ovate. Margin: Serrate. Apex: Acute to broadly acute. Base: Attenuate. Venation pattern: Pinnate. Length of mature leaf: Approximately 8.0 cm. Width of mature leaf: Approximately 3.5 cm. Texture of upper surface: Sparsely pubescent. Texture of lower surface: Sparsely pubescent on venation. Color of upper surface of young and mature foliage: Closest to but darker than 137A. Color of lower surface of young and mature foliage: Closest to 137B. Venation of upper and lower surface: 147C.

*Petioles.*—Length: Approximately 1.3 cm. Width: Approximately 2.0 mm. Texture: Sparsely pubescent. Color: 147C.

Flowering description:

*Flowering habit.*—'Balverevlu' flowers during late spring through summer under outdoor conditions.

*Lastingness of individual flower on the plant.*—Approximately 7 days.

Inflorescence description:

*General description.*—Type: Terminal raceme, self-cleaning. Fragrance: Faint. Height: Approximately 12.0 cm. Width: Approximately 1.7 cm. Quantity per plant: Approximately 50.

*Peduncle.*—Strength: Strong. Aspect: Erect. Length: Approximately 2.5 cm. Diameter: Approximately 1.5 mm. Texture: Densely pubescent. Color: 146B.

Flower description:

*General description.*—Type: Single, campanulate. Aspect: Outward. Quantity per inflorescence: Approximately 70.

*Bud.*—Rate of opening: Generally takes 3 to 4 days for bud to progress from first color to fully open flower. Quantity per inflorescence: Approximately 30.

*Bud just before opening.*—Shape: Oblong. Length: Approximately 5.0 mm. Diameter: Approximately 2.0 mm. Texture: Glabrous. Color: NN155D with N88B at apex.

*Corolla.*—Height: Approximately 8.0 mm. Diameter: Approximately 5.0 mm.

*Petals.*—Quantity: 4, in a single whorl. Appearance: Dull. Shape: Elliptic. Margin: Entire, wavy. Apex: Broadly acute. Base: Fused into tube. Length: Approximately 4.0 mm to 5.0 mm. Width: Approximately 2.0 mm to 3.0 mm. Texture of upper and lower surfaces: Glabrous. Color of upper and lower surfaces when first open: N89D. Color of upper and lower surfaces when fully open N89D to N89C.

*Corolla tube.*—Length: Approximately 3.0 mm. Diameter at tube opening: Approximately 2.0 mm. Texture of inner surface: Densely pubescent. Color of pubescence: NN155D. Texture of outer surface: Glabrous. Color of inner surface: NN155D. Color of outer surface: NN155D with a faint overlay of N89D.

*Caylx.*—Shape: Cupped. Length: Approximately 4.0 mm. Diameter: Approximately 3.0 mm.

*Sepals.*—Quantity per flower: 4. Shape: Lanceolate, fused at base. Apex: Acute. Length: Two larger sepals approximately 4.0 mm and two smaller sepals approximately 3.0 mm. Width of all sepals: Approximately 1.0 mm. Texture of upper and lower surfaces:

Moderately pubescent on margins only. Color of upper and lower surfaces: 137B with 146D at base.

*Pedicel.*—Strength: Strong, flexible. Aspect: Approximately 45° angle from peduncle. Length: Approximately 1.0 mm. Diameter: Approximately 0.5 mm. Texture: Densely pubescent with appressed and curled hairs. Color: 146B often tinted with 187A.

*Reproductive organs.*—Androecium: Stamen quantity: 2 per flower. Stamen length: Approximately 7.0 mm. Filament color: NN155D with a heavy overlay of N89D on upper half. Anther shape: Sagittate, dorsifixed. Anther length: Approximately 1.0 mm. Anther color: N92B. Pollen amount: Abundant. Pollen color: 2D. Gynoecium: Pistil quantity: 1 per flower. Pistil length: Approximately 9.0 mm. Stigma shape: Rounded. Stigma length: Less than 1.0 mm. Stigma color: N92B. Style length: Approximately 8.0 mm. Style color: N89D. Ovary diameter: Approximately 1.0 mm. Ovary color: 145C.

Seed and fruit production: Neither seed nor fruit production has been observed.

Disease and pest resistance: Resistance to pathogens and pests common to *Veronica* has not been observed.

What is claimed is:

1. A new and distinct cultivar of *Veronica* plant named 'Balverevlu', substantially as herein illustrated and described.

* * * * *